United States Patent
Wietelmann et al.

(10) Patent No.: US 8,956,991 B2
(45) Date of Patent: Feb. 17, 2015

(54) CONCENTRATED SOLUTIONS OF ALKALINE-EARTH METAL OXIDES IN APROTIC SOLVENTS AND METHOD FOR THE PRODUCTION THEREOF

(75) Inventors: Ulrich Wietelmann, Friedrichsdorf (DE); Ute Emmel, Frankfurt (DE); Jens Röder, Goslar (DE); Martin Steinbild, Frankfurt (DE); Kay Papstein, Goslar (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 13/376,672

(22) PCT Filed: Jun. 17, 2010

(86) PCT No.: PCT/EP2010/058550
§ 371 (c)(1),
(2), (4) Date: Feb. 27, 2012

(87) PCT Pub. No.: WO2010/146122
PCT Pub. Date: Dec. 23, 2010

(65) Prior Publication Data
US 2012/0149553 A1    Jun. 14, 2012

(30) Foreign Application Priority Data
Jun. 18, 2009    (DE) .......................... 10 2009 027 018

(51) Int. Cl.
*C08F 4/52*    (2006.01)
*C09K 3/00*    (2006.01)
*C07C 29/70*    (2006.01)
*C08F 10/00*    (2006.01)

(52) U.S. Cl.
CPC ................. *C07C 29/70* (2013.01); *C08F 10/00* (2013.01)
USPC ...................................... 502/171; 252/183.11

(58) Field of Classification Search
None
See application file for complete search history.

(56) References Cited

U.S. PATENT DOCUMENTS

| 4,748,283 A | 5/1988 | Kamienski |
| 6,734,134 B1 | 5/2004 | Gray et al. |
| 2009/0112027 A1 | 4/2009 | Dietz et al. |

FOREIGN PATENT DOCUMENTS

| EP | 0156 512 A1 | 10/1985 |
| EP | 1 031 580 A1 | 8/2000 |
| JP | 01-259003 | * 10/1989 |
| WO | WO 85/02176 | 5/1985 |
| WO | WO 2007/026016 A1 | 3/2007 |

* cited by examiner

*Primary Examiner* — Yun Qian
(74) *Attorney, Agent, or Firm* — Fulbright & Jaworski LLP

(57) ABSTRACT

A concentrated solution of mixed alkaline-earth alkoxide compounds $M(OCH_2R^6)_{2-x}(OR^7)_x$ and an aluminum compound $Al(OCH_2R^6)_{3-y}(OR^7)_y$, in aprotic solvents, wherein M is an alkaline-earth metal selected from among Mg, Ca, Ba, Sr; $OCH_2R^6$ is an alkoxide group comprising at least 3 and at most 40 C atoms and having a branch at the 2-position relative to the O-function, in other words $R^6$ is $CHR^8R^9$, wherein $R^8$, $R^9$ are alkyl groups $C_1$-$C_{18}$ independently of each other; $R_7$ is an alkyl group having 2-15 C atoms that is either linear or has a branch at ≥the 3-position; and the sum of x and y is a number between 0.01 and 0.8.

16 Claims, No Drawings

CONCENTRATED SOLUTIONS OF ALKALINE-EARTH METAL OXIDES IN APROTIC SOLVENTS AND METHOD FOR THE PRODUCTION THEREOF

This application is a §371 of PCT/EP2010/058550 filed Jun. 17, 2010, and claims priority from DE 10 2009 027 018.3 filed Jun. 18, 2009.

The invention relates to concentrated solutions of alkaline earth metal alkoxides in aprotic solvents, and a method for preparing same.

Magnesium alkoxides are necessary, among other things, for producing supported olefin polymerization catalysts of the Ziegler-Natta type. For this purpose, according to the document EP 1031580, for example, insoluble alkoxides such as magnesium ethoxide in the form of spherical particles are used, which are converted to the active form by reaction with titanium chloride or some other compound having titanium-halogen bonds, for example dicyclopentadienyl titanium dichloride ($Cp_2TiCl_2$):

$$Mg(OEt)_2 + Cp_2TiCl_2 \rightarrow Mg(OEt)_{2-x}Cl + Cp_2TiCl_{2-x}(OEt)_x$$

(x=0 to 2)

According to WO 85/02176, another option for producing supported Ziegler-Natta catalysts is to start with soluble magnesium alkoxides. While most magnesium alcoholates, such as the Mg salts of methanol, ethanol, propanol, isopropanol, tert-butanol, etc., are insoluble in aprotic solvents, the Mg compounds of primary alcohols having a branch at the 2-position have been found to be soluble in hydrocarbons. Thus, for example, the magnesium salts of 2-methyl-1-pentanol or of 2-ethyl-1-hexanol dissolve in cyclohexane in concentrations of 1.3 mol/L. In addition, according to WO 85/02176 mixed Mg alkoxides, i.e., those having two different alkoxide radicals $Mg(OR^1)(OR^2)$, may be soluble in hydrocarbons when the corresponding alcohol $R^1OH$ is a primary alcohol branched in the 2-position, and the corresponding alcohol $R^2OH$ is a secondary alcohol.

A disadvantage of hydrocarbon solutions which contain no other dissolved metal besides magnesium is their relatively high viscosities. In addition, it is not possible to prepare such solutions directly by reacting magnesium metal with the alcohol in the desired hydrocarbon without adding auxiliary agents, which have interfering effects. To allow a direct reaction at all, the magnesium metal must be activated, which may be achieved by etching with iodine. However, with this measure the speed of reaction is still very low, even when highly-reactive Mg powder is used. EP 0156512 describes the preparation of a diluted solution of magnesium-di-(2-ethylhexoxide) (MEHO) in dodecane, using iodine. At a reaction temperature of 145° C. a ten-hour reaction time is necessary, and the product is obtained in the form of a viscous solution. According to WO 2007/026016, another option for activating magnesium is to treat the alkaline earth metal with trialkylaluminum compounds. This method has the advantage that the product is not contaminated with iodine. However, the speeds of reaction are not satisfactory, and viscous products are obtained which have a relatively high degree of contamination with protic impurities, in particular free alcohol.

To avoid the extremely long reaction times, magnesium alcoholate solutions are therefore generally prepared from commercially available dialkylmagnesium compounds. However, this synthesis route has the disadvantage that a relatively expensive source of magnesium is used. Furthermore, a specific solvent is implicitly required, namely, saturated hydrocarbons: dialkylmagnesium compounds, for example dibutylmagnesium, butylethylmagnesium, and butyloctylmagnesium are commercially available only in saturated hydrocarbons such as hexane or heptane. In addition, during alcoholysis according to $$R^3R^4Mg + 2ROH \rightarrow Mg(OR)_2 + R^3H + R^4H,$$

saturated hydrocarbons $R^3H$ and $R^4H$, for example butane or octane, are unavoidably produced. Therefore, direct preparation of magnesium alcoholates in pure aromatic solvents such as toluene or ethylbenzene is not possible via the dialkylmagnesium route.

Another synthesis variant for preparing soluble alkaline earth alcoholates lies in the transalcoholization of insoluble alkaline earth alcoholates prepared from highly volatile alcohols (ethanol, for example) with a higher-boiling alcohol, such as the following:

$$Mg(OR^5)_2 + 2ROH \rightarrow Mg(OR)_2 + 2R^5OH$$

A disadvantage is the relatively high, cost-intensive level of effort for this method: the alcoholate $Mg(OR^5)_2$ must first be prepared from the volatile alcohol $R^5OH$ and magnesium metal, and isolated, then reacted with a less volatile alcohol, for example 2-ethylhexanol, and the volatile alcohol $R^5OH$ must then be removed, for example by distillation.

The relatively high viscosity of magnesium alkoxide solutions is caused by association phenomena. It is known from U.S. Pat. No. 6,734,134 that the viscosity may be reduced by adding alkylaluminum compounds. The preferred ratio of alkylaluminum compound to Mg alcoholate is between 0.001:1 and 1:1, preferably 0.01 to 0.1:1, and very particularly preferably 0.03 to 0.05:1.

A simple method is sought which, starting with an inexpensive source of magnesium and with a high space-time yield, results in less viscous, concentrated solutions of a magnesium alcoholate in aprotic, preferably aliphatic or aromatic, hydrocarbon solvents. A further aim is for the desired products to have the lowest possible content of interfering impurities such as iodine, and protic materials such as water and free alcohols, so that the products are suitable for producing Ziegler-Natta catalysts.

The object is achieved by providing mixed alkaline earth alkoxide compounds $M(OCH_2R^6)_{2-x}(OR^7)_x$ in a mixture with an aluminum compound $Al(OCH_2R^6)_{3-y}(OR^7)_y$ in aprotic solvents, wherein:

M is an alkaline earth metal selected from Mg, Ca, Ba, Sr;

$OCH_2R^6$ is an alkoxide radical composed of at least 3 and a maximum of 40 C atoms having a branch in the 2-position, relative to the O function; i.e., $R^6 = -CHR^8R^9$ where $R^8$, $R^9$ independently stand for alkyl radicals $C_1$-$C_{18}$;

$R^7$ is an alkyl radical containing 2-15 C atoms, which is either linear or has a branch at the 3- or higher position, relative to the position of the oxygen (O function); and the sum of x and y is a number between 0.01 and 0.8, preferably between 0.02 and 0.3, and particularly preferably between 0.03 and 0.2.

The aprotic solvent is, or contains, on the one hand, one or more aliphatic compounds containing 5 to 20 C atoms, whereby cyclic as well as open-chain compounds are possible. The following are preferred: cyclohexane, methylcyclohexane, hexane, heptane, octane, nonane, decane, dodecane, or decalin, as well as commercially available boiling cuts such as benzene fractions.

On the other hand, the aprotic solvent may contain or be composed of aromatics. The following are preferred: benzene, toluene, ethylbenzene, xylenes, and cumene.

In another embodiment of the invention, the alkaline earth alkoxide solution according to the invention may also contain polar aprotic solvents such as ether or tertiary amines.

The alcohol ($HOCH_2R^6$) which is branched in the 2-position is particularly preferably selected from the group composed of isobutanol, 2-methyl-1-pentanol, 2-ethyl-1-butanol, 2-ethyl-1-pentanol, 2-ethyl-4-methyl-1-pentanol, 2-propyl-1-heptanal, 2-methyl-1-hexanol, 2-ethylhexanol, and 2-ethyl-5-methyl-1-octanol, or any given mixture of at least two of the listed alcohols. The primary alcohol ($HOR^7$) is preferably selected from the group composed of ethanol, propanol, butanol, pentanol, hexanol, octanol, decanol, dodecanol, 3-methylbutan-1-ol, or any given mixture of at least two of the listed alcohols.

The products according to the invention are generally prepared as follows: Commercially available alkaline earth metal, preferably magnesium metal, which is preferably in the form of a powder, granules, or shavings, is placed in an anhydrous aprotic solvent, preferably aromatic or aliphatic hydrocarbons, in an agitator vessel which is inerted, i.e., dried and provided with a protective gas such as nitrogen or argon. An alkylaluminum compound, for example a trialkylaluminum such as triethylaluminum or tributylaluminum, an alkylaluminum hydride such as dibutylaluminum hydride, an alkylaluminum halide such as dibutylaluminum chloride, or an alkoxyaluminum compound such as diethylaluminum ethoxide is added, and stirring is performed for 5 minutes to 2 hours at 20 to 180° C., preferably 40 to 120° C. The optimal quantity of alkylaluminum compound depends on the quality of the alkaline earth metal, in particular the quality of the magnesium, and the quantity of alcohols added in the subsequent step. The molar ratio of alkylaluminum compound to the alcohols is generally between 0.0001 and 0.1 to 1, preferably between 0.001 and 0.07 to 1.

A branched alcohol $HOCH_2R^6$ and a primary alcohol $HOR^7$ which is unbranched or which has a branch at the 3- or higher position and contains 2-15 C atoms is then added. The addition may be carried out either in succession in any desired sequence, or in a mixture. The primary alcohol $R^7OH$ is preferably added first, then the branched $HOCH_2R^6$. The addition may be carried out at temperatures between 0 and 180° C., preferably between 40 and 140° C. The addition is very particularly preferably carried out at the boiling point of the solvent used; thus, in the case of toluene, for example, at approximately 110° C. The reaction time depends on the reactivity of the alkaline earth metal used, in particular the magnesium, and of the alcohol used, the stoichiometric ratio of alkaline earth metal, in particular magnesium, to the alcohols, and the reaction temperature, as well as the requirements for the end product, in particular the allowable residual content of free alcohol. When the alkaline earth metal, in particular the magnesium, is used in excess, preferably in 1 to 300% excess, particularly 10 to 100% excess, a reaction time of 1 to 6 hours is sufficient when the reflux procedure is used.

After the reaction is completed, which is identifiable by the cessation of the hydrogen flow, excess alkaline earth metal, in particular magnesium metal, which may be present is removed form the desired product solution. This may be carried out by decanting, filtration, or centrifugation.

The products prepared using the method according to the invention, depending on the concentration, are slightly viscous and contain a slight amount of water and free alcohol. The alkaline earth metal concentrations are preferably in the range of approximately 0.4 to 1.2 mmol/g, particularly preferably between 0.5 and 0.8 mmol/g. The viscosities, measured at room temperature, are generally less than 500 mPa s, preferably less than 250 mPa s, particularly preferably less than 200 mPa s. The content of protic impurities relative to the dissolved alkaline earth metal element is generally between 0.1 and 15 mol-%, preferably between 1 and 10 mol-%, relative to the alkaline earth content.

The content of dissolved aluminum relative to dissolved alkaline earth metal is in the range between 0.5 and 15 mol-%, preferably between 1 and 8 mol-%. The proportion of primary alcohol $HOR^7$, which is unbranched or which has a branch at the 3- or higher position and contains 2-15 C atoms, to the total alcohol content is between 0.5 and 40 mol-%, preferably between 1 and 20 mol-%, particularly preferably between 1.5 and 10 mol-%.

The products according to the invention are used for producing polymerization catalysts, in particular heterogenized polyolefin catalysts of the Ziegler-Natta type. They may also be used in organic synthesis, for example as bases.

EXAMPLES

All reactions were carried out in dry glass equipment inerted with argon. Commercially available magnesium shavings were used in an excess of 100% relative to the alcohol used. The magnesium was activated, i.e., prepared for reaction, as described in WO 2007/026016 A1, generally using approximately 2 mol-% of a trialkylaluminum compound relative to alcohol used.

Comparative Example 1

Preparation of magnesium-2-ethyl hexanolate in n-heptane without Addition of a Primary Alcohol $HOR^7$ which is Unbranched or which has a Branch at the 3- or Higher Position and Contains 2-15 C Atoms, as Described in WO 2007/026016 A1

14.9 g magnesium shavings and 437 g n-heptane were placed in a 0.5-L double-jacketed glass reactor equipped with a reflux condenser and a dropping funnel. 6.5 g of a 33% solution of tributylaluminum in cyclohexane was then injected. The mixture was heated to the boiling point, and 79.8 g 2-ethylhexanol was added dropwise over a period of 90 minutes. 1.04 L gas was evolved. After the dosing, the reactor contents were refluxed for an additional 225 min, resulting in further evolution of 3.1 L gas. Intense foaming of the reaction mixture was observed toward the end of the secondary reaction time.

After cooling to approximately 80° C., the dark gray suspension was filtered. 510 g of a viscous liquid was obtained which had a magnesium content of 0.28 mmol/g, corresponding to a conversion of 49% of the theoretical yield. The product solution also contained 0.025 mmol/g aluminum and 0.803 mmol/g protic impurities.

Example 1

Preparation of magnesium-2-ethyl hexanolate in n-heptane in the Presence of 1 mol-% n-octanol 13.5 g magnesium shavings and 300 g n-heptane were placed in a 0.5-L double-jacketed glass reactor equipped with a reflux condenser and a dropping funnel. 4.8 g of a 25% solution of triethylaluminum in toluene was then injected. The mixture was heated to the boiling point, and a mixture of 73.0 g 2-ethylhexanol and 0.73 g n-octanol was added dropwise over a period of 150 minutes. 4.9 L gas was evolved. After the dosing, the reactor contents were refluxed for an additional 190 minutes, resulting in further evolution of 2.0 L gas. Hardly no foam formation was observed.

After cooling to approximately 80° C., the dark gray suspension was filtered. 363 g of a viscous liquid was obtained which had a magnesium content of 0.66 mmol/g, corresponding to a conversion of 96% of theoretical. The product solution also contained 0.027 mmol/g aluminum and 0.108 mmol/g protic impurities.

Example 2

Preparation of magnesium-2-ethyl hexanolate in n-heptane in the Presence of 6 mol-% ethanol 13.5 g magnesium shavings and 300 g n-heptane were placed in a 0.5-L double-jacketed glass reactor equipped with a reflux condenser and a dropping funnel. 4.8 g of a 25% solution of triethylaluminum in toluene was then injected. The mixture was heated to the boiling point, and a mixture of 73.0 g 2-ethylhexanol and 1.46 g ethanol was added dropwise over a period of 135 minutes. 6.0 L gas was evolved. After the dosing, the reactor contents were refluxed for an additional 105 minutes, resulting in further evolution of 0.55 L gas, without foaming.

After cooling to approximately 80° C., the dark gray suspension was filtered. 377 g of an almost clear liquid was obtained which had a magnesium content of 0.72 mmol/g, corresponding to a conversion of 99% of theoretical. The product solution also contained 0.028 mmol/g aluminum and 0.046 mmol/g protic impurities.

Comparative Example 2

Preparation of magnesium-2-ethyl hexanolate in toluene without Addition of a Primary Alcohol HOR$^7$ which is Unbranched or which has a branch at the 3- or Higher Position and Contains 2-15 C atoms, according to WO 2007/026016 A1

20.4 g magnesium shavings and 600 g toluene were placed in a 1.0-L double-jacketed glass reactor equipped with a reflux condenser and a dropping funnel. 9.0 g of a 21% solution of triethylaluminum in toluene was then injected, the mixture was heated to the boiling point, and 116 g 2-ethylhexanol was added dropwise over a period of 52 minutes. 3.25 L gas was evolved. After the dosing, the reactor contents were refluxed for an additional 900 minutes, resulting in further evolution of 4.7 L gas. Extremely intense foaming was observed.

After cooling to approximately 80° C., the dark gray suspension was filtered. 680 g of a viscous liquid was obtained which had a magnesium content of 0.50 mmol/g, corresponding to a conversion of 87% of theoretical. The product solution also contained 0.030 mmol/g aluminum and 0.189 mmol/g protic impurities.

Example 3

Preparation of magnesium-2-ethyl hexanolate in toluene in the Presence of 8.7 mol-% ethanol 20.3 g magnesium shavings and 450 g toluene were placed in a 0.5-L double-jacketed glass reactor equipped with a reflux condenser and a dropping funnel. 9.7 g of a 25% solution of triethylaluminum in toluene was then injected, and the mixture was heated to the boiling point. 3.39 g ethanol, and subsequently 109.7 g 2-ethylhexanol, were then added dropwise over a period of 2 hours. 9.1 L was evolved. After the dosing, the reactor contents were refluxed for an additional 160 minutes, resulting in further evolution of 0.84 L gas, without foaming.

After cooling to approximately 80° C., the reaction mixture was filtered. 565 g of an almost clear liquid was obtained which had a magnesium content of 0.73 mmol/g, corresponding to a conversion of 100% of theoretical. The product solution also contained 0.037 mmol/g aluminum and 0.077 mmol/g protic impurities.

Further test results are summarized in Table 1:

Comparative examples 1 and 2 were carried out according to the technical teaching of WO 2007/026016 A1; i.e., the magnesium was activated with trialkylaluminum solutions, and the reactions with the branched alcohol HOCH$_2$R$^6$ were carried out at the boiling point.

When the reaction was carried out for at least 5 hours in heptane in the absence of a primary alcohol HOR$^7$ which is unbranched or which has a branch at the 3- or higher position and contains 2-15 C atoms, a conversion of approximately only 50% to the desired metal alcoholate product was observed. Intense foaming was observed. The method product also had an extremely high content of undesired protic impurities: 0.803 mmol/g, corresponding to 287 mol-% relative to dissolved magnesium. In the presence of only 1 mol-% n-octanol, over approximately the same time period a marked increase in the reaction conversion to 96% was achieved, as shown in Example 1. Consequently, the content of protic impurities was very markedly decreased; the foam formation was significantly reduced relative to the comparative experiment. Despite almost twice the metal alcoholate concentration, the product viscosity was actually slightly lower.

When the proportion of primary alcohol HOR$^7$ which is unbranched or which has a branch at the 3- or higher position and contains 2-15 C atoms was increased to 6 mol-%, as shown in Example 2, an almost quantitative conversion was observed, even after a 4-hour reaction time. The obtained solution showed only a very low concentration of protic compounds in the form of water and free alcohols, and the solution was only very slightly viscous (195 mPa s).

Similar observations were made when aromatic solvents were used (toluene in Example 3 and Comparative example 2). In the presence of primary alcohol HOR$^7$ which is unbranched or which has a branch at the 3- or higher position and contains 2-15 C atoms (see Example 3, in which ethanol was used), the speed of reaction was significantly increased and the product quality was improved.

TABLE 1

| Comparative example | Solvent | ROH (mol-%) | Reaction time (min) | Mg (mmol/g) | Protic impurities (mmol/g)/(mol-%)* | Conversion (% of theoretical) | Viscosity (mPa s) |
|---|---|---|---|---|---|---|---|
| 1 | n-Heptane | 1 (n-Octanol) | 340 | 0.66 | 0.108/16 | 96 | 830 |
| 2 | n-Heptane | 6 (Ethanol) | 240 | 0.72 | 0.046/6.4 | 99 | 195 |
| Comp. 1 | n-Heptane | ./. | 315 | 0.28 | 0.803/287 | 49 | 850 |

TABLE 1-continued

| Comparative example | Solvent | ROH (mol-%) | Reaction time (min) | Mg (mmol/g) | Protic impurities (mmol/g)/(mol-%)* | Conversion (% of theoretical) | Viscosity (mPa s) |
|---|---|---|---|---|---|---|---|
| 3 | Toluene | 8, 7 (Ethanol) | 280 | 0.73 | 0.077/11 | 101 | 100 |
| Comp. 2 | Toluene | ./. | 952 | 0.50 | 0.189/38 | 87 | 540 |

*Relative to dissolved magnesium

The invention claimed is:

1. A solution comprising:
a mixed alkaline earth alkoxide compound of $M(OCH_2R^6)_{2-x}(OR^7)_x$; and
an aluminum compound of the formula $Al(OCH_2R^6)_{3-y}(OR^7)_y$ in an aprotic solvent; wherein:
M is an alkaline earth metal selected from Mg, Ca, Ba, Sr;
$OCH_2R^6$ is an alkoxide radical composed of at least 3 and a maximum of 40 carbon atoms having a branch in the 2-position, relative to the oxygen function; wherein $R^6$ is —$CHR^8R^9$, wherein $R^8$ and $R^9$ independently stand for alkyl radicals $C_1$-$C_{18}$; wherein
$R^7$ is an alkyl radical containing 2-15 carbon atoms, which has a branch at the 3- or higher position, relative to the oxygen function; and
wherein the sum of x and y is a number between 0.01 and 0.8.

2. A solution according to claim 1, wherein the alkaline earth metal concentration is in the range of 0.4 to 1.2 mmol/g.

3. A solution according to claim 1, wherein the room temperature-viscosities are generally less than 500 mPa s.

4. A solution according to claim 1, wherein the content of protic impurities relative to the dissolved alkaline earth metal element is generally between 0.1 and 15 mol-%.

5. A solution according to claim 1, wherein the content of dissolved aluminum relative to dissolved alkaline earth metal is in the range between 0.5 and 15 mol-%.

6. A method for preparing a solution according to claim 1 comprising the steps of reacting an alkaline earth metal activated with an alkylaluminum compound in an aprotic solvent, and then adding an alcohol which is branched in the 2-position and with an alcohol $HOR^7$ which has a branch at the 3- or higher position and contains 2-15 C atoms.

7. A method according to claim 6, wherein the alkylaluminum compound is selected from the group consisting of trialkyl, alkylalkoxy, and alkyl halide compound.

8. A method according to claim 6, wherein the aprotic solvent is a hydrocarbon.

9. A method according to claim 6, wherein the aprotic solvent is aliphatic.

10. A method according to claim 6, wherein the aprotic solvent is selected from the group consisting of cyclohexane, methylcyclohexane, hexane, heptane, octane, nonane, decane, dodecane, decalin, a benzene fraction, benzene, toluene, ethylbenzene, xylenes, and cumene.

11. A method according to claim 6, wherein the aprotic solvent is aromatic.

12. A method according to claim 6, wherein the reaction is carried out at temperatures between approximately 0 and 180° C.

13. A method according to claim 6, wherein as the alcohol $HOCH_2R^6$ which is branched in the 2-position, isobutanol, 2-methyl-1-pentanol, 2-ethyl-1-butanol, 2-ethyl-1-pentanol, 2-ethyl-4-methyl-1-pentanol, 2-propyl-1-heptanol, 2-methyl-1-hexanol, 2-ethylhexanol, and 2-ethyl-5-methyl-1-octanol, or any given mixture of at least two of the listed alcohols is used, and as an alcohol which is branched in the 2-position and with an alcohol $HOR^7$ which has a branch at the 3- or higher position and contains 2-15 carbon atoms.

14. A method according to claim 6, wherein the alcohol $HOR^7$ is added first, then the alcohol $HOCH_2R^6$ which is branched in the 2-position is added.

15. A method of using a solution according to claim 1 for producing polymerization catalysts that is heterogenized polyolefin a catalyst.

16. A method comprising conducting an organic synthesis with a solution according to claim 1.

* * * * *